United States Patent [19]

Merchant et al.

[11] 3,976,447

[45] Aug. 24, 1976

[54] REMOVAL OF HYDROGEN FLUORIDE FROM GASEOUS MIXTURE BY ABSORPTION ON ALKALINE EARTH METAL FLUORIDE

[75] Inventors: Dhirendra Ranchhoddas Merchant, Paducah; Jimmie Ray Hodges, Benton, both of Ky.

[73] Assignee: Pennwalt Corporation, Philadelphia, Pa.

[22] Filed: Mar. 11, 1975

[21] Appl. No.: 560,907

Related U.S. Application Data

[63] Continuation-in-part of Ser. No. 354,715, April 26, 1973, which is a continuation-in-part of Ser. No. 153,839, June 16, 1971, abandoned.

[52] U.S. Cl............................................ 55/71; 55/74; 423/483; 423/484; 423/488
[51] Int. Cl.$^2$.......................................... B01D 53/02
[58] Field of Search.................... 423/483, 484, 488; 55/22, 71, 74, 388

[56] References Cited

UNITED STATES PATENTS

| 2,426,558 | 8/1947 | Long et al............................ 55/71 X |
| 2,526,776 | 10/1950 | Smith et al............................ 55/71 |
| 3,798,875 | 3/1974 | Morris .................................... 55/22 |

*Primary Examiner*—John Adee

[57] ABSTRACT

A gaseous mixture containing up to 20% of hydrogen fluoride and other gases inert to alkaline earth metal fluorides is passed in contact with particulate anhydrous alkaline earth metal fluoride prepared by the fluorination of anhydrous alkaline earth metal chloride in the absence of water. After the anhydrous alkaline earth metal fluoride has taken up the desired amount of hydrogen fluoride, up to its absorption capacity, the hydrogen fluoride is removed therefrom, e.g. by heat regeneration, and the alkaline earth metal fluoride is reused to absorb additional hydrogen fluoride from said gaseous mixtures.

16 Claims, No Drawings

REMOVAL OF HYDROGEN FLUORIDE FROM GASEOUS MIXTURE BY ABSORPTION ON ALKALINE EARTH METAL FLUORIDE

This application is a continuation-in-part of copending application Ser. No. 354,715 filed Apr. 26, 1973 which is a continuation-in-part of application Ser. No. 153,839 filed June 16, 1971, now abandoned.

This invention relates to the removal of hydrogen fluoride (HF) gas from gaseous mixtures containing up to about 20% of HF, based on the weight of the gaseous mixture, and other gases inert to alkaline earth metal fluorides, in the absence of water. The gaseous mixture is passed in contact with particulate, anhydrous alkaline earth metal chloride in the absence of water. Preferably, the anhydrous alkaline earth metal chloride is fluorinated by contact with a dry gaseous mixture inert to alkaline earth metal chloride except for a minor proportion of HF therein. Alternatively, a dry gas containing at least a major proportion of HF or a dry fluorine gas can be used to obtain the particulate, anhydrous alkaline earth metal fluoride employed in the process of this invention.

After absorbing HF gas in an amount ranging up to the absorption capacity of the specified anhydrous alkaline earth metal fluoride, the flow of the gaseous mixture is terminated or diverted and the absorbed HF is removed from the alkaline earth metal fluoride, preferably by desorption with heat. The regenerated alkaline earth metal fluoride is then reused in the HF removal process. Liquids, other than aqueous liquids, can be tolerated in the gaseous mixture as long as they do not collect in the process vessels in amounts sufficient to obscure significant amounts of the surface area of the absorption material.

The term "absorption" is used herein to include chemisorption, adsorption and absorption although the term "absorption" will be used herein to describe the process.

The alkaline earth metal compounds employed for this invention are the calcium, barium or strontium chlorides and fluorides in their anhydrous form. Calcium is the preferred alkaline earth metal and will be primarily used hereinafter to further demonstrate the invention. The anhydrous forms of alkaline earth metal chlorides are prepared by drying the hydrates at temperatures suitable to remove water of hydration.

The gaseous mixtures included herein which contain HF in amounts up to about 20%, based on the weight of the gaseous mixture, and other gases inert to alkaline earth metal fluorides include mixtures of HF, hydrogen chloride (HCl) and volatile organic gases obtained from various manufacturing processes; HF and HCl mixtures substantially free of other gases; HF and fluorine gas with and without other inert gases; dry air containing traces of HF; waste gases from petroleum alkylation processes involving anhydrous HF; waste gases in the aluminum metal and ceramic industries containing traces of HF; etc.

The process of this invention is especially useful for the treatment of HF — contaminated gaseous hydrogen chloride encountered as a by-product in fluorinated hydrocarbon synthesis. More specifically, in commerical processes for the production of fluorinated hydrocarbons (such as $CCl_3F$, $CCl_2F_2$, $CClF_3$, $CHCl_2F$, $CHClF_2$, $CHF_3$, $CH_3CClF_2$, $CH_3CCl_2F$, $CH_3CF_3$, $CCl_2FCClF_2$, $CClF_2CClF_2$, and the like which products are useful as refrigerants, blowing agents and aerosol propellants) involving the fluorination with HF of chlorinated hydrocarbons, such as $CCl_4$, $CHCl_3$, $CH_3CCl_3$, and $CCl_2=CCl_2$, a large amount of hydrogen chloride containing varying but significant proportions of hydrogen fluoride is obtained as a by-product, which hydrogen chloride by-product cannot be discarded for obvious economic and ecological reasons. However, this contaminated hydrogen chloride must be purified so that the HCl can be used in industrial applications, for example, in oxychlorination reactions, food processing, pickling of steel, and in the treatment of brine used in electrolytic chlorine production, the presence of HF in such systems being intolerable.

F. R. Lowdermilk, U.S. Pat. No. 3,140,916, has suggested one method for removing HF contamination wherein a gaseous mixture of hydrogen chloride and hydrogen fluoride is passed through an aqueous solution of calcium chloride, whereby the hydrogen fluoride reacts with the calcium chloride in solution to form calcium fluoride as a precipitated solid that is recoverable by filtration. This multi-step aqueous technique has several serious disadvantages stemming from the problems in dealing with an aqueous system comprised of HCl, $CaCl_2$, and $CaF_2$. This mixture is highly corrosive and the precipitated $CaF_2$-in-water mixture forms an abrasive slurry, both conditions being very injurious to plant equipment. Lowdermilk also mentions that aluminum oxide has been used as an absorption agent for removal of HF from HCl.

A simple and economical process for removing HF impurity from a gaseous mixture of hydrogen chloride has been disclosed in D. F. Merchant's copending application Ser. No. 354,715, Apr. 26, 1973, a continuation-in-part of Ser. No. 153,839, filed June 16, 1971. This copending application concerns the method of passing gaseous HCl containing HF in contact with substantially anhydrous, solid, particulate calcium chloride. It was noted, during the operation of this process, that the calcium fluoride, obtained in situ therein via the conversion of $CaCl_2$, is endowed with the capability to absorb up to somewhat over 50% of its own weight of HF. Moreover, this calcium fluoride maintains the size, shape, appearance, free-flowing and other easy-handling characteristics of the precursor calcium chloride.

W. L. Colvin, in AEC Report K 1117, discloses the use of calcium fluoride as a sorbent for hydrogen fluoride, the said calcium fluoride being prepared by direct fluorination of calcium sulfate. However, he only observed a very low loading for the level breakthrough of HF. With the present invention, an average loading of about 20% of HF on $CaF_2$ under normal operation is obtained.

Colvin likewise reports a surface area of 129 square meters/gram for his material. This calcium fluoride material employed herein has surface area of about 12–17 square meters/gram. Thus, the process of this invention provides the unobvious and unexpected result of removing more HF per unit weight of absorbent with considerably less surface area.

Laboratory tests showed that naturally occurring calcium fluoride does not have the ability to absorb a significant amount of HF. Naturally occurring calcium fluoride could absorb only about 5 to 6% by weight HF before breakthrough while the calcium fluoride made by reacting calcium chloride and HF can absorb about 20% HF by weight before breakthrough under the same conditions of flow, temperature and pressure.

The term "breakthrough", as used herein, is explained as follows:

When HF is being absorbed by passing a gas containing it through an absorption medium, the outlet concentration of HF in the gas is generally fairly uniform or increasing at a slow rate. When the outlet concentration of HF in the gas begins to increase at a rapid rate (as compared to previous rates), breakthrough has occurred.

Table I below summarizes measurement made on the surface area and absorption of HF on calcium fluoride ($CaF_2$) prepared by passing anhydrous HF through a bed of anhydrous calcium chloride ($CaCl_2$) in the absence of water until the $CaCl_2$ was converted to $CaF_2$ as determined by analysis of the solids. The absorbed HF was then desorbed by heat and air purge.

TABLE I

PHYSICAL DATA

| SAMPLE | COMPOUND | SPECIFIC SURFACE AREA SQ. METERS/GRAM* | % HF ABSORBED ON $CaF_2$ |
|---|---|---|---|
| I | $CaF_2$ | 13.5 | 40 |
| II | $CaF_2$ | 16.5 | 40 |
| III | $CaF_2$ (natural fluorspar) | 1.8 | 10 |
| IV | $CaCl_2$ (anhydrous) | 2.0 | — |

*Determined by the American Chemical Societies B. E. T. Method (Brunauer, Emmet & Teller)

These results show a marked change in physical structure of the compound $CaCl_2$ when reacted with HF to form $CaF_2$. Also shown in Sample III is natural fluorspar, $CaF_2$. Its surface area is on the order of that of the $CaCl_2$. It absorbed only 10% HF under the same conditions as Samples I and II.

The HF absorbed by the "synthetic" calcium fluoride produced as above described can be stripped off by suitable heating means, and the thus regenerated $CaF_2$ will again serve as an absorbent for additional HF present in the gaseous mixture.

The HF containing gaseous mixture treated in accordance with this invention to effect HF removal may contain from 0.3 to about 20 weight percent HF, based on total weight of the gaseous mixture. The regenerative-recycle system embodied herein is particularly suited, however, to those mixtures containing moderately large amounts of HF, e.g., from about 0.5 to about 6.0 weight percent. In a more useful application of this process, there may be present in admixture with an HF-containing gaseous hydrogen chloride mixture up to about 70 but preferably up to about 60 weight percent, based on the total weight of the gaseous mixture, of one or more volatile halogenated hydrocarbons, i.e., chlorofluorohydrocarbons, chlorohydrocarbons, and fluorohydrocarbons for example, $CCl_4$, $CCl_3F$, $CCl_2F_2$, $CClF_3$, $CHCl_2F$, $CHClF_2$, $CHF_3$, $CHCl_3$, $CH_3CClF_2$, $CH_3CCl_2F$, $CCl_2FCClF_2$, $CClF_2CClF_2$, $CCl_2CCl_2$, and the like. Such volatile halogenated hydrocarbons do not interfere with the HF absorption and undergo no discernible change from contact with the $CaF_2$. The product HCl can be separated from these organic constitutents either by distillation to provide an anhydrous HCl gas or by absorption in water to provide an aqueous HCl solution. In the latter technique, the small amount of organic material that is absorbed in the aqueous acid may be easily removed by blowing with air or other gas or by absorption on activated carbon or molecular sieves.

The absorption tower used in carrying out the process of the invention can be initially charged with a suitable bed of particulate $CaF_2$ prepared from the substantially anhydrous calcium chloride as described above, or in the preferred embodiment, is charged with the anhydrous $CaCl_2$ which is then normally converted to the $CaF_2$ when the feed stream of HF-containing gaseous HCl is passed in contact therethrough. The particulate calcium fluoride can range from powdery to granular type to pellets, that is, having an average particle size over the broad range of 0.025 to 0.375 inch (0.0625 – 0.937 cm.). In the preferred embodiment, however, the calcium fluoride is in pellet form, e.g., having a particle size of from about 0.25 to about 0.375 inch (0.625–0.937 cm.).

The temperature at which the gaseous hydrogen chloride mixture is contacted with the particulate $CaF_2$ may be in the range of about 60°F (15.5°C) to about 130°F (54.5°C), preferably from about 70°F (21°C) to 115°F (45°C). It is desirable to maintain the temperature of contact above the dew point of the gaseous mixture to prevent any organics present therein from condensing in the reactor column. Pressures may vary from essentially atmospheric up to about 250 psig (18 atm.), depending on other process conditions. Because the system is essentially anhydrous, exotic materials of construction are not required and the absorption tower and auxiliary piping and equipment can be of ordinary carbon steel, corrosion thereof not being an abnormal problem.

The term anhydrous as used herein means a substance containing less than 1000 and preferably less than 200 parts by weight of water per million (p.p.m.) parts of substance. Likewise, the term in the absence of water signifies a process carried out with a gas containing less than 1000 p.p.m. of water.

An advantage provided by this invention, in addition to simplicity of operation and low operating costs, is the general efficiency of absorption of HF, even at relatively high through-put rates. For example, after processing an HCl-organic gaseous mixture originally containing about 18% HF in accordance with this invention, the product gas will usually contain less than 0.05 weight percent HF, although flow rates of the feed gas may vary over the range of from about 1.0 to about 100 pounds per hour per square foot of particulate $CaF_2$, measured at standard conditions of 15 psia pressure and 70°F temperature. Stated in different terms, the foregoing results of HF absorption are obtained using periods of contact of the gaseous HCl mixture with the particulate calcium fluoride (also referred to as retention time) of from about 20 to about 600 seconds. The quality of the product gas (amount of HF contamination) is, of course, influenced to some extent by these flow rates.

The feed of the dry gaseous mixture to the particulate $CaF_2$ bed is continued until an appropriate amount of HF is absorbed therein. This amount may be on the order of about 50% of the weight of the $CaF_2$ at the maximum; however, it is apparent that one factor in absorption efficiency is the amount of free surface remaining in the $CaF_2$ solids; therefore, the operator who desires a comparatively more pure HCl product can terminate the HCl gas feed, or divert the feed to a fresh tower before the $CaF_2$ has absorbed the maximum amount. The so-called "spent" $CaF_2$ solids are then regenerated by desorbing, that is, stripping the solids of absorbed HF. This is conveniently accomplished by any of a number of conventional methods: (1) external heating of the absorption column to around 225° to 350°F; (2) heating the column to 200°F or higher and passing an inert gas, such as nitrogen, air or anhydrous HF through the solids; or (3) passing an inert gas, heating to 350°F or higher, through the solids. The desorbed HF is recovered and can be used in hydrofluorination processes.

The "regenerated" bed of $CaF_2$ solids after cooling is used for another cycle of treatment of HF-containing gaseous mixture, and after HF absorption has reached the desired level, as discussed above, the regeneration cycle is repeated. The number of complete cycles for which a specific $CaF_2$ charge may be employed is limited by the actual physical breakdown of the charge due to the heating and cooling cycles. Therefore, the number of cycles is limited by the allowable pressure drop of the system. At that point, the absorbent $CaF_2$ should be replaced with a fresh bed of the like or, preferably, substantially anhydrous, particulate $CaCl_2$. The spent $CaF_2$ solids (which may have lost its good physical properties because of physical degradation) is recovered from the bottom of the tower. This can be used as a raw material for preparing hydrofluoric acid in an $H_2SO_4$-reactor kiln.

The process of this invention is clarified and illustrated by the following examples:

EXAMPLE I

A by-product gaseous mixture obtained from the process of hydrofluorinating chloroform is comprised of hydrogen chloride containing about 60% organics (halogenated hydrocarbons, mostly $CHClF_2$ with lesser amounts of $CHCl_2F$, $CHCl_3$ and $CHF_3$) and 10.3 % hydrogen fluoride, based on the weight of HCl present. The gas mixture is passed through a one inch diameter steel column filled with 3.3 feet of particulate calcium fluoride, at 15 psia and 90°F, superficial gas velocities ranging from 0.15 to 1.5 ft/min, equivalent to retention times on the order of 110 to 330 seconds. The $CaF_2$ has a particle size of 3/16 to ¼ inch and is obtained from the process of contacting anhydrous $CaCl_2$ of said particulate size range with a stream of substantially the same composition as noted above in the absence of water.

The HF content of the gaseous HCl mixture is reduced from 10.3% to 0.38%, based on HCl content, equivalent to an HF removal efficiency of 96.4%. A total of 0.36 cu. ft. of the feed gas is passed through the bed until the HF absorbed therein is 14% by weight. The calcium fluoride is regenerated (absorbed HF stripped off) by heating the column to 350°F with electrical heating tape. The $CaF_2$ is then ready to treat further quantities of the feed HCl gas mixture in like manner.

EXAMPLE II

A by-product gaseous mixture obtained frm the hydrofluorination of methyl chloroform is comprised of HCl containing about 54% volatile halogenated hydrocarbons (mostly $CH_3CClF_2$ with lesser amounts of $CH_3CCl_2F$ and $CH_3CF_3$) and 18% HF, based on the weight of the HCl. The gas mixture is passed through a two inch diameter steel column containing a 2.6 ft. bed of $CaF_2$ as embodied in this invention. The $CaF_2$ is made by passing the above described gaseous mixture through anhydrous $CaCl_2$ of particle size ⅛ to ¼ inch diameter pellets. After the $CaCl_2$ is converted completely to $CaF_2$, the absorbed HF is driven off by suitable means and the $CaF_2$ is ready for reuse as an absorbent. Typical operating conditions are as follows: pressure is 2 psig and the temperature of contact about 100°F. The system is subject to four cycles of operation, the $CaF_2$ being regenerated between the cycles by the method of the previous example. The results are tabulated as follows:

TABLE II

| CYCLE NUMBER | FT.³ OF FEED GAS TREATED | HF IN HCl FEED | MIXTURE PRODUCT | HF REMOVAL EFFICIENCY | GAS VELOCITY, FT./MIN. | CONTACT TIME SECONDS | HF ABSORBED ON CaF₂, END OF CYCLE |
|---|---|---|---|---|---|---|---|
| 1 | 1.07 | 18% | 0.4% | 98% | 0.2 | 780 | 3% |
| 2 | 2.51 | 18% | 1.4% | 92.2% | 2.4 | 65 | 7% |
| 3 | 5.73 | 18% | 4.7% | 74% | 1.3 | 120 | 16% |
| 4 | 6.44 | 18% | 10.1% | 44% | 1.65 | 95 | 18% |

At the end of the fourth cycle, the $CaF_2$ is removed from the column as a free-flowing solid without any appreciable change in size, shape or appearance.

EXAMPLE III

A gaseous HCl mixture similar to that of Example II is passed through a two ft. diameter column having a bed of 4.5 feet of particulate $CaF_2$ prepared by passing the HCl mixture similar to that in Example II through anhydrous $CaCl_2$ until the $CaCl_2$ is fully converted to $CaF_2$, then driving off the absorbed HF by suitable means, leaving $CaF_2$. Operation is at 100°F and 155 psig. Gas flow is 2 CFM with a velocity of about 0.6 ft./min. and a contact time of 450 seconds. Two cycles are run in the test with regeneration of the $CaF_2$ between cycles being accomplished by heating the column externally to 400°F and passing a hot 350°F nitrogen purge through the $CaF_2$ to drive off absorbed HF. The results are summarized in the following table:

TABLE III

| CYCLE NO. | HF IN HCl FEED | MIXTURE PRODUCT | HF REMOVAL EFFICIENCY | HF ABSORBED ON CaF₂, END OF CYCLE |
|---|---|---|---|---|
| 1 | 15.6% | 2.3% | 85% | 3% |
| 2 | 15.6% | 9.3% | 40% | 10% |

EXAMPLE IV

The following table shows the results of a series of absorption runs using a 6 inch diameter column by 5.5 ft. bed depth of $CaF_2$ operating on a mixture of HF, HCl, $CH_3CClF_2$, and other chlorinated fluorocarons in minor amounts or a mixture of HF, HCl, $CHClF_2$ and other chlorinated fluorocarbons in minor amounts. All absorption tests we made on the same charge of $CaF_2$.

TABLE IV

| RUN NO. | GAS FLOW CFM | VELOCITY FT./MIN. | CONTACT TIME SECONDS | OPER. PRESS. PSIG | BED TEMP. °F (AVG.) | HF IN HCl FEED | HF REMOVAL EFFICIENCY | AVERAGE BED LOADING % HF ON CaF₂ |
|---|---|---|---|---|---|---|---|---|
| 1 | 0.80 | 4.00 | 82.5 | 50 | 142 | 19.69% | 47.23% | 17.0% |
| 2 | 0.19 | 0.93 | 306.9 | 150 | 120 | 16.87% | 61.18% | 21.0% |
| 3 | 0.32 | 1.59 | 207.5 | 55 | 120 | 18.75% | 62.37% | 17.0% |
| 4 | 0.52 | 2.60 | 126.9 | 155 | 125 | 18.12% | 33.72% | 19.0% |
| 5 | 0.72 | 3.60 | 91.7 | 50 | 100 | 18.75% | 25.00% | 31.8% |
| 6 | 0.19 | 0.93 | 306.9 | 150 | 95 | 14.69% | 12.00% | 38.0% |

The data herein relating to HF content of gases and solids was obtained by standard analytical techniques. The bed samples were obtained by "coring" of the bed.

EXAMPLE V

The following table shows the results of a series of absorption runs using a 2 ft. diameter column with a 4.5 ft. CaF₂ bed depth operating on the gases described in Example 4 above. All absorption tests were made on the same charge of CaF₂.

TABLE V

| RUN NO | GAS FLOW CFM | VELOCITY FT./MIN. | CONTACT TIME SECONDS | OPER. PRESS. PSIG | BED TEMP. °F (AVG.) | HF IN HCl FEED | HF REMOVAL EFFICIENCY | AVERAGE BED LOADING % HF ON CaF₂ |
|---|---|---|---|---|---|---|---|---|
| 1 | 5.93 | 1.90 | 142.1 | 100 | 90 | 18.75% | 50.00% | 13.0% |
| 2 | 12.41 | 3.95 | 68.4 | 52 | 70 | 20.63% | 49.09% | 14.5% |
| 3 | 4.86 | 1.55 | 174.2 | 155 | 93 | 13.13% | 59.52% | 9.0% |
| 4 | 2.01 | 0.64 | 421.9 | 155 | 100 | 15.63% | 59.60% | 8.0% |
| 5 | 4.83 | 0.54 | 500.0 | 55 | 95 | 19.69% | 59.05% | 7.0% |
| 6 | 1.69 | 0.54 | 500.0 | 85 | 95 | 15.94% | 44.71% | 3.0% |
| 7 | 4.77 | 1.52 | 177.6 | 150 | 112 | 15.38% | 36.00% | 35.0% |

EXAMPLE VI

Regeneration of the CaF₂ used in the series of Example V was performed as follows:

1. The 2 ft. diameter bed was heated to 350°F by applying heat to the outside of the 2 ft. diameter column. They dry nitrogen, at the rate of 1 SCFM per sq. ft. of bed area, was heated to 400°F by a tube heater and passed through the bed. The HF on the CaF₂ was desorbed and collected in a chilled vessel. The CaF₂ was completely desorbed with less than 0.5% HF on CaF₂ remaining. This method was used for the regenerations of the majority of the runs.

Another regeneration procedures is as follows:

2. The 2 ft. diameter CaF₂ bed was heated externally, by applying heat to the outside of the 2 ft. diameter column, to 350°F. Then a vacuum of 25 inches of Hg was placed on the 2 ft. diameter bed. The HF was desorbed from the CaF₂ and recovered in a chilled receiver. The residual HF on the CaF₂ was less than 0.5% by weight. This method was used for the last two runs of Example V. In both these cases, the desorption was made in the same direction as the HF was originally adsorbed on the CaF₂, that is, cocurrent with the absorption stream.

EXAMPLE VII

Regeneration of the CaF₂ contained in the 6 inch diameter column was performed as follows:

The 6 inch diameter column was jacketed so that 150 psig steam could be applied to the vessel externally. The CaF₂ bed containing absorbed HF was heated to about 350°F, then air at about 150°F was introduced at a rate varying from 0.25 to 1.0 SCFM per sq. ft. of CaF₂ bed area. This air was passed counter current to the direction of the absorption of the HF, i.e., if the HF was absorbed from the organic stream by passing the organic stream from the bottom of the CaF₂ bed through the top of the CaF₂ bed, then the desorbing air was passed from top to bottom of the CaF₂ bed. The CaF₂ bed was desorbed to less than 0.5% HF based on CaF₂ weight.

EXAMPLE VII

Barium chloride dihydrate ($BaCl_2 \cdot 2H_2O$) was mixed with calcium chloride dihydrate ($CaCl_2 \cdot 2H_2O$) in the ratio of 9 parts $BaCl_2 \cdot 2H_2O$ and 1 part $CaCl_2 \cdot 2H_2O$. A wet cake of the above was pressed into a billet under 3000 psi hydraulic pressure. The billet was then dried at 300°F for 16 hours. The billets were then crushed, screened, and fines less than ¼ inch were discarded.

The ¼ inch pieces were placed in a 2 I.D. × 24 inches long steel pipe modified to allow sampling at 8 inches length, 16 inches length, and the outlet. Six Hundred fifty-five grams of the above described mix were placed in the 2 inches I. D. × 24 inches long tube. The tube was placed in a chlorofluoro carbon gas stream containing approximately 3% by volume HF, 36% by volume HCl, and 61% by volume organics. After 45 hours, the tube was removed and analyzed. Residence time was about 200 seconds. Analysis after 45 hours showed 29.6% by weight HF absorbed on the solids. Analysis of the solids showed no residual chlorides in the solids (i.e., complete conversion).

The table below shows the percentage amount of hydrogen fluoride removed from the gas stream at various times beginning at 2 hours up to 45 hours.

TABLE VI

| | ppm, HF | | % HF |
|---|---|---|---|
| Hours | Inlet | Outlet | Removed |
| 2 | 12,000 | 71 | 99.4 |
| 5 | 12,500 | 84 | 99.3 |
| 8 | 13,500 | 1,620 | 87.5 |
| 18 | 16,000 | 1,710 | 89.3 |
| 24 | 17,400 | 1,200 | 93.0 |
| 37 | 12,300 | 7,800 | 36.6 |
| 40 | 12,300 | 12,000 | 2.5 |
| 45 | 13,000 | 11,400 | 12.0 |

Retention time: 200 secs.
Grams Sample: 655 (as $BaCl_2$ + $CaCl_2$)
Grams Sample: 546.3 (as $BaF_2$ + $CaF_2$)
Grams HF Absorbed: 161.7

TABLE VI-continued

| Hours | ppm, HF Inlet | Outlet | % HF Removed |
|---|---|---|---|

Grams HF Removed: 301.6 (total)

The barium fluoride pellets as prepared above may be regenerated in accordance with one of the procedures of Example VI or Example VII. Thereafter, the anhydrous barium fluoride may be used in absorption runs as set forth in Examples IV or V.

What is claimed is:

1. A method for the removal of hydrogenfluoride from a gaseous mixture containing up to about 20% of hydrogen fluoride, based on the weight of the gaseous mixture, and other gases inert to alkaline earth metal fluorides, said method comprising passing said gaseous mixture fluorocarbons contact with particulate, anhydrous alkaline earth metal fluoride prepared by the fluorination of particulate anhydrous alkaline earth metal chloride in the absence were water, said method being carried out in 2. absence of water whereby hydrogen fluoride is absorbed on said anhydrous alkaline earth metal fluoride.

2. The method of claim 1 wherein the alkaline earth metal is calcium.

3. The method of claim 1 wherein the alkaline earth metal is barium.

4. The method of claim 1 wherein the fluorination of anhydrous alkaline earth metal chloride is obtained by the reaction of anhydrous alkaline earth metal chloride and hydrogen fluoride which is present as a component in a gaseous mixture with other gases inert to said alkaline earth metal chloride.

5. The method of claim 4 wherein said gaseous mixture includes hydrogen chloride.

6. The method of claim 5 wherein said gaseous mixture includes volatile halogenated hydrocarbons.

7. The method of claim 6 wherein said alkaline earth metal is calcium.

8. The method of claim 1 wherein the anhydrous alkaline earth metal fluoride having hydrogen fluoride absorbed thereon is periodically regenerated by removal of the hydrogen fluoride absorbed thereon and the regenerated anhydrous alkaline earth metal fluoride is reused to absorb hydrogen fluoride from said gaseous mixture passing in contact therewith.

9. The method of claim 8 wherein said gaseous mixture includes hydrogen chloride.

10. The method of claim 9 wherein said gaseous mixture includes volatile halogenated hydrocarbons.

11. The method of claim 10 wherein fluorination of particulate, anhydrous alkaline earth metal chloride is obtained by the reaction of said chloride with said hydrogen fluoride present in said gaseous mixture.

12. The method of claim 8 wherein the alkaline earth metal is calcium.

13. The method of claim 10 wherein the alkaline earth metal is calcium and the average particle size in the largest dimension of the particulate, anhydrous calcium fluoride ranges betwen 0.025 and 0.375 inch.

14. The method of claim 13 wherein the temperature at which said gaseous mixture contacts said anhydrous calcium fluoride ranges between about 60°F and about 130°F.

15. The method of claim 14 wherein the ambient pressure at which said gaseous mixture contacts said anhydrous calcium fluoride ranges from about atmospheric up to about 250 psia.

16. The method of claim 1 wherein the anhydrous alkaline earth metal chloride is prepared by dehydration of the alkaline earth metal chloride hydrate before fluorination to the alkaline earth metal fluoride.

\* \* \* \* \*

UNITED STATES PATENT OFFICE
CERTIFICATE OF CORRECTION

Patent No. 3,976,447        Dated August 24, 1976

Inventor(s) Dhirendra Ranchhoddas Merchant, Jimmie Ray Hodges

It is certified that error appears in the above-identified patent and that said Letters Patent are hereby corrected as shown below:

Claim 1
READS

1. A method for the removal of hydrogenfluoride from a gaseous mixture containing up to about 20% of hydrogen fluoride, based on the weight of the gaseous mixture, and other gases inert to alkaline earth metal fluorides, said method comprising passing said gaseous mixture fluorocarbons contact with particulate, anhydrous alkaline earth metal fluoride prepared by the fluorination of particulate anhydrous alkaline earth metal chloride in the absence were water, said method being carried out in 2. absence of water whereby hydrogen fluoride is absorbed on said anhydrous alkaline earth metal fluoride.

SHOULD READ

1. A method for the removal of hydrogen fluoride from a gaseous mixture containing up to about 20% of hydrogen fluoride, based on the weight of the gaseous mixture, and other gases inert to alkaline earth metal fluorides, said method comprising passing said gaseous mixture in contact with particulate, anyhdrous alkaline earth metal fluoride prepared by the fluorination of particulate anhydrous alkaline earth metal chloride in the absence of water, said method being carried out in the absence of water whereby hydrogen fluoride is absorbed on said anhydrous alkaline earth metal fluoride.

Signed and Sealed this

Twenty-third Day of November 1976

[SEAL]

Attest:

RUTH C. MASON
Attesting Officer

C. MARSHALL DANN
Commissioner of Patents and Trademarks